United States Patent [19]

Koyama et al.

[11] Patent Number: 4,551,307

[45] Date of Patent: Nov. 5, 1985

[54] ANALYTICAL ELEMENT

[75] Inventors: Mikio Koyama; Shozo Kikugawa; Kenichiro Okaniwa, all of Hino, Japan

[73] Assignee: Konishiroku Photo Industry Co., Ltd., Tokyo, Japan

[21] Appl. No.: 381,794

[22] Filed: May 25, 1982

[30] Foreign Application Priority Data

May 28, 1981 [JP] Japan .................................. 56-82372

[51] Int. Cl.[4] ........................ G01N 33/52; G01N 33/54
[52] U.S. Cl. ........................................ 422/56; 422/57; 435/805
[58] Field of Search ............................. 422/56, 57, 58; 435/805

[56] References Cited

U.S. PATENT DOCUMENTS

| | | | |
|---|---|---|---|
| 3,811,840 | 5/1974 | Bauer et al. | 422/56 |
| 4,029,597 | 6/1977 | Neisius et al. | 422/56 X |
| 4,258,001 | 3/1981 | Pierce et al. | 422/56 |
| 4,286,964 | 9/1981 | Seed | 422/56 X |
| 4,292,272 | 9/1981 | Kitajima et al. | 422/57 |
| 4,330,299 | 5/1982 | Cerami | 422/56 X |
| 4,361,648 | 11/1982 | Shuenn-tzong | 422/56 X |
| 4,430,436 | 2/1984 | Koyama et al. | 422/56 |

*Primary Examiner*—Arnold Turk
*Attorney, Agent, or Firm*—Frishauf, Holtz, Goodman & Woodward

[57] ABSTRACT

There is disclosed an analytical element comprising a light-transmissive and liquid-impermeable support and at least one developing layer of a fibrous structure containing at least one kind of interactive composition reactive with a component in a liquid sample, characterized in that the fiber constituting the developing layer of a fibrous structure and the interactive composition are bonded to each other by a compound having a reactive group. A quantitative analysis of a specific component in a liquid sample can effectively be carried out by using the analytical element according to this invention.

23 Claims, No Drawings

ANALYTICAL ELEMENT

This invention relates generally to analytical chemistry, particularly to an analytical element for analysis of a predetermined specific component in a liquid. More particularly, it pertains to a quantitative analytical element for assay of a specific component in a liquid sample.

As a method for analysis of a component in a liquid sample, there has been known an analytical system employing test papers or test strips. As test papers or test strips used in such an analytical system, there have been proposed those prepared by dipping an absorptive carrier such as a filter paper in an analytical reagent solution followed by drying, as disclosed in, for example, U.S. Pat. No. 3,050,373 or U.S. Pat. No. 3,061,523. This test strip enables measurement by dipping in a liquid sample of analyte and then withdrawing to read the color change or density change on the test strip with naked eyes or by means of an instrument such as densitometer.

These test strips are easy in handling and useful in giving instantly the test results. But, these test strips comprising reagents carried in absorptive carriers suffer from various vital defects, and therefore their applications are still limited to qualitative or semi-quantitative analysis.

For overcoming these defects, there has been developed an analytical element as disclosed in U.S. Pat. No. 3,992,158. These elements have a reagent layer containing analytical reagents and a spreading layer comprising an isotropically porous, non-fibrous medium laminated on a transparent support.

The developing layer disclosed in said Patent, however, has essentially only brittle strength, tending to be broken at a high percentage, and stable supply of these films is difficult. Also, from aspects of preparation, it is required to control severely the conditions for coating, and constant void volume (porosity) can hardly be obtained if such conditions are no satisfied.

The object of the present invention is to provide an analytical element having excellent quantitative characteristics without requiring skilled operational techniques.

The present inventors have made extensive studies and were successful in overcoming the drawbacks as mentioned above by use of an analytical element having the following constitution.

That is, the analytical element according to the present invention comprises a light-transmissive and liquid-impermeable support and at least one developing layer of a fibrous structure containing at least one kind of interactive composition reactive with a component in a liquid sample, characterized in that the fibers constituting said developing layer of a fibrous structure and said interactive composition are bonded to each other by a compound having a reactive group.

As the fibers constituting the developing layer of a fibrous structure of the present invention, there may be included natural macromolecular fibers such as natural celluloses or derivatives thereof, silk, wool, etc., synthetic macromolecular fibers such as polyolefins (e.g., polyethylene, polypropylene, etc.), polyamides (e.g., nylon), polyvinyl alcohol fibers, and others. When the above various fiber materials are to be used as porous developing layers, they may either be loose fibers which are randomly entangled with each other, as disclosed in Japanese Provisional Patent Publication No. 24576/1981, of fabrics having regularity, as disclosed in Japanese Provisional Patent Publication No. 72047/1980. Further, a dispersion of loose fibers may be coated and dried to form an available product.

In particular, when a fiber dispersion as mentioned above is used, there may be chosen either a single kind or two or more kinds with any desired size, generally of 50 to 325 mesh, preferably 100 to 320 mesh, more preferably 200 to 300 mesh, according to the JIS standard screen.

The compound having reactive groups to be used in the present invention is a compound having a group which is reactive with amino groups or carboxyl groups in an interactive composition and thus capable of forming a chemical bonding. As the reactive group possessed by such a compound, there may be included, for example, an epoxy group, an aldehyde group, a formyl group, an aziridyl group, a hydroxymethyl group, an isocyanate group, a thiol group, a carbamoyl group, a vinylsulfonyl group and precursors thereof. A vinyl monomer having a group selected from those as mentioned above may preferably be used in the present invention.

The compound having reactive groups is contained in said developing layer preferably in an amount of 0.1 to 100% by weight, most preferably in an amount of 0.5 to 85% by weight.

As a monomer having an epoxy group, there may be mentioned, for example, glycidyl acrylate, glycidyl methacrylate, allyl glycidyl ether, 4-vinylcyclohexane monoepoxide, etc. A monomer having an aziridyl group may be exemplified by aziridylethyl methacrylate, 1-ethylenesulfonyl aziridine, 1-ethylenecarbonyl aziridine, aziridylethyl acrylate, etc. Typical examples of a monomer having a formyl group are acrolein and methacrolein.

A monomer having a hydroxymethyl group may include, for example, N-methylol-acrylamide, N-methylol-methacrylamide, N-methylol-diacetoneacrylamide, and the like.

Typical examples of a monomer having an isocyanate group are vinyl isocyanate and allyl isocyanate. Examples of a monomer having a thiol group are vinyl thiol, p-thiol styrene, m-thiol styrene, vinyl benzyl thiol and acetyl derivatives of these. As a monomer having a carbamoyl group, there may be included, for example, acrylamide, methacrylamide, maleinamide, diacetone acrylamide, etc.

Among the monomers having various reactive groups as mentioned above, typical examples of the monomers having an epoxy group, an aziridyl group, a hydroxylmethyl group or a carbamoyl group may be inclusive of those mentioned hereinabove.

Examples of monomers having other reactive groups are as follows. As a monomer having a carboxyl group, there may be mentioned acrylic acid, methacrylic acid, itaconic acid, maleic acid, itaconic acid half-ester, maleic acid half-ester, etc. A monomer having an amino group may be exemplified by aminostyrene, N,N-dimethylaminoethyl acrylate, N,N-dimethylaminoethyl methacrylate.

Typical examples of a monomer having a methoxy group are methoxyethyl acrylate, ethoxyethyl acrylate, methoxyethyl methacrylate, ethoxyethyl methacrylate, and the like. As a monomer having $-COOC_4H_9(t)$ group, there may be included tert-butyl acrylate, tert-butyl methacrylate. Examples of a monomer having a ureido group are ureidoethyl acrylate, ureidoethyl methacrylate, ureidovinyl ether (e.g., those represented by the formula $CH_2=CHONRCONHR'$, wherein R represents a hydrogen atom or a methyl and R' a hydrogen atom or a lower alkyl such as methyl or ethyl). As a monomer having a hydroxyl group, there may be mentioned 2-hydroxyethyl acrylate, 2-hydroxyethyl methacrylate, 2-hydroxypropyl methacrylate, 2-hydroxypropyl acrylate, etc. A monomer having a haloethylsulfonyl group may be exemplified by chloroethylsulfonylethyl methacrylate, bromoethylsulfonylethyl methacrylate, etc. A typical example of a monomer having a vinylsulfonyl group is vinylsulfonylethyl methacrylate. Examples of a monomer having an active methylene containing group are acryloyl acetone and methacryloyl acetone. As a monomer having a carboxymethoxymethyl group, there may be mentioned, for example, N-carboxymethoxymethyl acrylamide and N-carboxymethoxymethyl methacrylamide.

In the present invention, it is possible to introduce the reactive groups reactive with an interactive composition in various ways. As an example of a preferred method for the introduction of the reactive groups of the present invention, there may be mentioned graft polymerization of a monomer.

Graft polymerization techniques may include, for example, a method in which a graft polymerization initiator (for example, ammonium cerium (IV) nitrate, etc.) and a macromolecular polymer having a tendency to be oxidized are used in combination. The macromolecular polymer having a tendency to be oxidized to be used in the present invention may include cellulose and cellulose derivatives, silk, wool and polyvinyl alcohol fibers as mentioned above. The surface grafting will proceed by allowing the aforesaid fibers according to the present invention to react in a non-solvent in the presence of a graft polymerization initiator and a monomer having a reactive group.

As another preferred example of the graft polymerization method, there may be mentioned radiation graft polymerization. This method involves irradiation of a high energy electromagnetic wave such as γ-ray, electron beam or UV-ray on a macromolecular polymer thereby to form radicals in the polymer chains of the macromolecular polymer, at which radicals as polymerization initiation sites graft polymerization is carried out. Radiation polymerization may generally be classified broadly into the simultaneous irradiation method and the pre-irradition method.

According to the simultaneous irradiation method, monomers are irradiated in the presence of a macromolecular polymer and radicals formed primarily on the monomers. On the other hand, according to the pre-irradiation method, a macromolecular polymer is previously irradiated to form radicals on the polymer, and thereafter the polymer is contacted with monomers either in liquid phase or gas phase to perform graft polymerization.

Among the radiation graft polymerization methods as mentioned, when UV-ray with a lower energy is to be employed, there may be employed a method in which readily cleavable groups are introduced into fibers, a method in which a sensitizer is used in combination or a method in which a chain transfer of photopolymerization is utilized.

As another method for introduction of reactive groups, there may be mentioned a low temperature plasma polymerization in which a plasma formed by an inert gas such as argon is utilized. Further, there may also be employed still another method as mentioned below. That is, the fibers to be employed in the present invention may be impregnated with a monomer or a solution thereof, followed by polymerization.

These methods may be contemplated along the same line as conventional suspension polymerization or emulsion polymerization. When the fibers impregnated with a monomer provide the place for polymerization and an oil-soluble polymerization initiator is employed, the resultant system is similar to suspension polymerization, while the reaction will proceed according to a polymerization mechanism of emulsion polymerization when a water-soluble polymerization initiator is employed.

Other than the above radical polymerization initiators, there may also be employed radiation polymerization, photopolymerization or others to give favorable results.

In accordance with the above methods, it is also possible to include pigments, dyes or other compounds in the polymer. For example, there may be included rare earth chelates as disclosed in European Pat. No. 2963, fluorescent blocking pigments or dyes such as Paliofast Blue ® (BASF), Sol Fast Methyl Violet ® (Sherwin Williams Co.), etc.

Other than the monomers having the reactive group as mentioned above, it is also possible to use other copolymerizable monomers, provided that they do not interfere with the object of the present invention.

Examples of other preferable monomers to be copolymerized with the monomers having reactive groups as described above are set forth below.

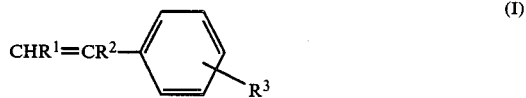

(I)

wherein each $R^1$ and $R^2$, which can be the same or different, represents a non-interfering substituent such as a hydrogen atom, a halogen atom, or a substituted or unsubstituted, amino-free alkyl or aryl group having 1 to 10 carbon atoms and $R^3$ represents a hydrogen atom, a halogen atom, or a substituted or unsubstituted, amino-free aliphatic or aromatic group having 1 to 10 carbon atoms. As aliphatic or aromatic groups, there may be included alkyl groups, alkoxy groups, aryl groups and aryloxy groups.

Typical examples of the monomers represented by the formula (I) are styrene, vinyltoluene, vinylbenzyl chloride, t-butylstyrene, etc.

$$CHR^6=CR^4-COOR^5 \qquad (II)$$

wherein $R^6$ has the same meaning as $R^1$ in the formula (I), $R^4$ represents a hydrogen atom or a methyl and $R^5$ represents an aryl, an alkyl, an alkaryl or aralkyl group, each having 1 to 10 carbon atoms.

(III) Polymerizable unsaturated nitrile monomers such as acrylonitrile and methacrylonitrile.

(IV) Interparticle crosslinking monomers having two addition-polymerizable groups such as divinylbenzene, N,N-methylene-bis(acrylamide), ethylene diacrylate and ethylene dimethacrylate.

By copolymerization of a suitable combination of these monomers with the aforesaid monomers having reactive groups, it is possible to constitute a compound having a reactive group according to the present invention, namely an organic macromolecular polymer having a reactive group. In the present invention, the monomer units having reactive groups may preferably be contained in an amount of 0.1 to 30% by weight in said organic macromolecular polymer unit, particularly 0.5 to 20% by weight. The monomers of the formulae (I), (II) and (III) to be copolymerized with the monomers having reactive groups may be contained in amounts of 0 to 99.5% by weight based on said macromolecular polymer units; and the monomer represented by the formula (IV) may be contained in an amount of 0 to 10% by weight, preferably 0 to 5% by weight based on said organic macromolecular polymer unit.

Said organic macromolecular polymer may be contained preferably in an amount of 0.2 to 200% by weight of said developing layer of fibrous structure, more preferably 0.5 to 150% by weight.

As described above, the fibers having introduced monomers having reactive groups according to various methods can not only immobilize an interactive composition by chemical bonding through the reactive groups, but also permit formation of chemical bondings between the remaining reactive groups which have not participated in the chemical bonding with the interactive composition or between such remaining reactive groups and certain groups in a binder or desirable adjacent layers, thereby not only increasing the mechanical strength of the developing layer of fibrous structure of the present invention, but also greatly enhance adhesion to the adjacent layers.

The fibers to be used in the present invention may be chemically bound with an interactive composition through the reactive groups introduced previously as mentioned above to give an analytical element which can effectively be employed. The interactive composition refers comprehensively to all compositions which can undergo reaction or catalytic action with a predetermined component in a liquid sample to give a detectable change. These can release, produce, or otherwise provide within an analytical element a detectable change through chemical activity, catalytic activity (formation of an enzyme-substrate complex), immunogenic activity (antigen-antibody reaction) and any other form of electrical, chemical or physical interaction. The aforesaid change is directly or indirectly indicative of the presence and/or concentration of a desired analyte, or a reaction or decomposition product of the analyte.

Preferably, the detectable change that is produced is radio-metrically detectable. Radiometric detection refers to detection by use of electromagnetic radiation measuring techniques such as fluorimetry, colorimetry, radioactive counting, and phosphorimetry.

As will be appreciated, among the various components that can be present in interactive composition are colorimetrically detectable dyes, pigments, and complexes; fluorimetrically detectable dyes, pigments and complexes; phosphorescent tags; radioactive tags; chemical reagents; antigens; haptens; immunoreagents such as antibodies and antigen-antibody complexes; enzymes; and precursors of the foregoing components.

The interactive composition as described above can form chemical bonding rapidly with fibers having reactive groups, thereby preventing undesirable migration of the interactive composition within an analytical element.

The fibers having chemically bound the interactive composition of the present invention can be formed into a developing layer of a fibrous structure according to various methods.

That is, in case of using a fibrous material having previously formed a layer such as filter paper, woven fabric or nonwoven fabric, it may be provided on one side of a support of an analytical element by such a means as pressure bonding.

On the other hand, said structural layer can be formed by coating of a dispersion of loose fibers. In this case, even in said structural layer formed from a dispersion having the fibers alone dispersed, the reactive groups are not participating in the chemical bonding with the interactive composition can be bound with each other to form a strong layer.

As an alternative method, a small amount of a hydrophilic colloidal substance can be used as a binder together with the fibers of the present invention as mentioned above to form a strong developing layer of the present invention. In this case, the hydrophilic colloidal substance employed may preferably be one having a group capable of chemically bonding with the reactive groups introduced into the fibers of the present invention. Typical examples may include, gelatin, polyvinyl alcohol and the like.

As still another method, it is also possible to use a small amount of a polymer latex as an adhesive. Such a polymer latex adhesive may include those as disclosed in Japanese Provisional Patent Publication No. 90859/1980, more preferably those polymer latices containing monomers having the reactive groups of the present invention.

In the former case, the adhesive acts to adhere the fibers of the present invention through thermal fusion, while in the latter case through mutual chemical bonding between reactive groups.

The binder or polymer latex adhesive to be applied in the developing layer of fibrous structure of the present invention may be contained in an amount less than 20% by weight of the fibers, preferably less than 10% by weight.

The analytical element having an interactive composition chemically bonded directly to the developing layer of fibrous structure of the present invention can effectively be used for fluid samples, particularly biological fluid samples containing a number of macromolecular substances. That is, when a predetermined component in a fluid sample and a macromolecular substance form a complex, such a complex will frequently remain stagnant in a porous developing layer. The complex does not readily disperse and is held within the layer in which such a complex is intended to undergo an analytical reaction, for example, a reagent layer. In accordance with the constitution of the present invention, all or a part of the analytical reaction may be performed in said developing layer.

Also, in case of immunological proteins, the reaction may be performed within a porous developing layer and thus there can be provided a more effective analytical element.

The analytical elements according to the present invention containing the aforesaid developing layer of fibrous structure can have any one of a variety of different configurations. It may have one or more of the developing layer of fibrous structure of the present invention, or alternatively a suitable combination of the developing layer of fibrous structure with any of a variety of functional layers, reagent containing layers and members, as exemplified by the reagent layer, the filtration layer, the reflection layer and the subbing layer as disclosed in U.S. Pat. No. 3,992,158, the radiation-blocking layer as disclosed in U.S. Pat. No. 4,042,335, the barrier layer as disclosed in U.S. Pat. No. 4,066,403, the registration layer as disclosed in U.S. Pat. No. 4,144,306, the migration-inhibition layers as disclosed in U.S. Pat. No. 4,166,093, the scintillation layer as disclosed in U.S. Pat. No. 4,127,499, the scavenger layer as disclosed in Japanese Provisional Patent Publication No. 90859/1980 and the destructive pod-shaped member as disclosed in U.S. Pat. No. 4,110,079, to constitute the analytical element adapted to accomodate the object of the present invention.

The analytical element of the present invention may have said developing layer of fibrous structure preferably in a thickness of 50 to 500 $\mu m$, more preferably to 100 to 350 $\mu m$ provided on a light-transmissive and liquid-impermeable support.

Useful support materials of the present invention include polymeric materials such as cellulose acetate, poly(ethylene terephthalate), polycarbonates and polyvinyl compounds (such as polystyrenes), glass, metal and paper. A support of choice of any particular element will be compatible with the intended mode of detection.

The support to be used in the present invention may have a thickness which is not particularly limited, but preferably a thickness of 50 to 500 $\mu m$, more preferably 50 to 350 $\mu m$.

In preparing the analytical element of this invention, the individual layers can be performed and thereafter laminated prior to use or maintained as separate layers until brought into fluid contact with the element is placed in use. Layers preformed as separate members, if coatable, can advantageously be coated from solution or dispersion on a surface from which the layer can be physically stripped when dried. However, a convenient procedure which can avoid problems of multiple stripping and lamination steps when contiguous layers are desired, is to coat an initial layer on a stripping surface or a support, as desired, and thereafter to coat successive layers directly on or beside those previously coated.

The analytical element having the developing layer of fibrous structure of this invention can be coated by the dip coating method, the air knife method, the curtain coating method or the extrusion coating method with the use of a hopper as disclosed in U.S. Pat. No. 2,681,294. If desired, it is also possible to use the method as disclosed in U.S. Pat. No. 2,761,791 and U.K. Pat. No. 837,095 for simultaneous coating of two or more layers.

Elements of the present invention can be adapted for use not only in the field of clinical chemistry, but in other fields of chemical analysis. In addition, by utilizing the function of holding a certain amount of liquid within a certain area of the film, the element of the present invention can be associated with other functional layers (e.g., layers of photographic elements).

Analytical elements of the present invention are very advantageous for use in clinical testing of body fluids, such as blood, blood serum, lymph and urine. In particular, blood serum is conventionally used in analysis of blood. But the analytical element can be conveniently applicable for analysis of any of whole blood, blood serum and blood plasma.

When whole blood is used, a radiation-blocking layer or other reflecting layer may be provided, if necessary, in order to avoid interference of detecting radiation by the blood cells. Of course, if it is desired to observe the color of blood cells directly, such as in a haemoglobin analysis, no such reflecting layer is necessary.

After the analytical result is obtained as a detectable change, by use of the analytical element of the present invention, it is measured by reflection spectrophotometry, transmission spectrophotometry, fluorescence spectrophotometry or scintillation counting, corresponding the various detectable changes. The thus obtained values of measurement can be utilized for determination of the unknown quantity of analyte with reference to the calibration curve previously prepared.

Immunoassay is a well-recognized technique for qualitative or quantitative assay of antibodies and antigens. The basis for all immunoassay techniques is the unique, immunological phenomenon whereby a specific antibody recognizes and binds to a specific antigen.

Typical examples of immunoassay are radioimmunoassay, enzymeimmunoassay and fluorescenceimmunoassay.

The antibodies, antigens to be used in these immunoassays and preparation techniques of label antigens or lablel antibodies, immunoassay techniques and principles are described in detail in textbooks, such as "Radioimmunoassay" ed. by Minoru Irie, Kodansha (1974), "Enzymeimmunoassay" ed. by Eiji Ishikawa, Tadashi Kawai and Kiyoshi Miyai, Igaku Shoin (1978).

Most currently available techniques for performing the immunoassay as mentioned above suffer from various disadvantages as shown below:

(I) Relatively large volumes (0.1 to 1.0 ml) of test liquid may be necessary compared to conventional chemical and blood assays typically using 10 to 200 $\mu l$ of liquid sample.

(II) Time-consuming incubation (several hours or overnight) of the test mixture is required.

(III) After incubation, it is necessary to perform physical separation of bound antigen-antibody conjugate and unbound antigens or antibodies.

(IV) Many steps are necessary and must be performed individually and separately for completion of the assay (including sample addition, incubation, separation, quantitation of label).

But the use of the analytical element of this invention to conduct immunoassay overcomes many of the above drawbacks. It will be understood, however, that other than the immunoassay based on the antigen-antibody reaction as mentioned above, an immunoassay based on an antigen-antibody displacement interaction as described in German OLS No. 28 01 455 is also applicable for the analytical element of the present invention.

In addition, an amount of the antibody for the labelled antigen is incorporated and immobilized in an analytical element, preferably within a layer thereof having a layer of a coherent particulate structure. Such immobilization can be accomplished by adsorption or chemical bonding to the surface of the organic polymer particle units of the bound particulate structure. The liquid sample to be analyzed for unknown antigen is then brought into contact with the element in the presence of the labelled antigen. The labelled antigen can be associated with the immunoassay element in one of several ways including, among others:

(1) direct addition of the labelled antigen to the liquid sample (containing unlabelled antigen) which is then applied to the immunoassay element for analysis;

(2) separate addition of the labelled antigen and the liquid sample to the immunoassay element including (a) addition of the labelled antigen just prior to or after addition of the liquid sample as well as (b) addition of the labelled antigen to the element followed by drying and then rewetting the element upon addition of the liquid sample; or (3) incorporation of the labelled antigen in the immunoassay element so that analysis can be initiated simply by application of the liquid sample.

For example, the labelled antigen can be incorporated in a separate reagent layer of the element or the same layer of the element containing the immobilized antibody. In any case, when the labelled antigen is incorporated in the element, care should be taken to maintain the labelled antigen apart from the immobilized antibody so that premature binding of labelled antigen to antibody is avoided.

When the liquid sample is brought into contact with the immunoassay element in the presence of the associated, labelled antigen as noted above, the labelled antigen and the unlabelled antigen (present in the sample and representing the unknown to be determined) compete for binding to the antibody which is present immobilized in one layer of the element. Useful methods of measurement to determine the presence and/or concentration of unlabelled antigen that can then be employed include: (A) detecting the unbound, labelled antigen that has migrated into a second layer of the element, e.g., a registration layer, or (B) detecting the bound, labelled antigen which binds to the immobilized antibody. In either method, the amount of unlabelled antigen (i.e., the analyte) in the liquid sample can be determined based on the detected concentration of labelled antigen.

The present invention is illustrated in further detail by referring to the following Examples, by which the present invention is not limited at all.

EXAMPLE 1

Introduction of reactive groups into cellulose

To a suspension of 20 g of a powdery filter paper C (300 mesh or more, produced by Toyo Roshi Co., Ltd.) in 200 ml of an aqueous acrolein solution, there were added 0.143 g of ammonium cerium (IV) nitrate and 1.0 ml of 1N-nitric acid, and the reaction was carried out at 85° C. for 5 hours. After completion of the reaction, the acrolein-grafted powdery filter paper was separated by filtration, washed with distilled water until there was no odor of acrolein and dried.

Immobilization of an enzyme onto the acrolein-grafted powdery filter paper

Into 100 ml of a phosphate buffer of pH 7.4, there was added 20 g of the above powdery filter paper having graft polymerized acrolein thereon, and 30 mg of glucose-oxidase (8000 units) and 60 mg of peroxidase (6000 units) were added. The mixture was stirred at 4° C. for 72 hours to carry out the reaction, then subjected to filtration, washed with 500 ml of a phosphate buffer of pH 7.4, subsequently with 1000 ml of an aqueous 0.15N sodium chloride solution.

Preparation of analytical element for glucose analysis

On a transparent poly(ethyleneterephthalate) support of a thickness of about 180 μm which had been subjected to under-coating, there was coated a mixture having the following composition:

| | |
|---|---|
| The above powdery filter paper having immobilized enzyme | 180 mg/100 cm² |
| Triton X-100 (Rohm & Haas Co.) | 8 mg/100 cm² |
| 2-(3-bromo-5-methoxy-4-hydroxyphenyl)-4,5-bis(4-methoxyphenyl)imidazole | 16 mg/100 cm² |
| Deionized gelatin | 0.72 mg/100 cm² |

The above element was buffered to pH 5.9 with NaH₂PO₄ to provide an analytical element. On the above analytical element, each 10 μl of 5% aqueous bovine serum albumin solutions containing 50, 75, 125 and 250 mg/dl of glucose, respectively, and each 10 μl of three kinds of human serums with glucose concentrations of low level, normal level and high level, were spotted, followed by incubation at 37° C. for 10 minutes, for quantitative testing of the analytical element. As the result, it was observed that there are good differences between the respective glucose concentration levels.

EXAMPLE 2

Introduction of acrolein into polypropylene fibers

A polypropylene fiber was finely divided into pieces of 300 mesh or less and 20 g thereof was irradiated by an electron beam at a total dosage of 5.5 Mrad by means of ICT type electron beam accelerating device. Immediately, the treated fibers were added into a benzene solution containing 10% by weight of acrolein, and after replacement with nitrogen, graft polymerization was carried out at 50° C. for 10 hours. After completion of the reaction, the reaction mixture was filtered and washed repeatedly with methanol. Grafted acrolein percentage: 6.8%.

Immobilization of an enzyme onto the acrolein-grafted polypropylene fibers

The above acrolein-grafted polypropylene fiber (20 g) was added into 200 ml of a phosphate buffer of pH 7.4, followed by addition of 3000 units of cholesterolesterase and 2000 units of cholesteroloxidase. Then, the reaction was carried out at 4° C. under stirring for 115 hours, and then filtered and washed with 500 ml of a phosphate buffer of pH 7.4 and 1000 ml of an aqueous 0.15N sodium chloride solution.

Preparation of analytical element for cholesterol analysis

The layers shown below were successively coated on a transparent undercoated poly(ethyleneterephthalate) support of a thickness of 180 μm.

| | |
|---|---|
| Reagent layer | |
| Deionized gelatin | 215 mg/100 cm² |
| Peroxidase | 70 units/100 cm² |
| 1,7-Dihydroxynaphthalene | 6.6 mg/100 cm² |
| 4-Aminoantipyrine hydrochloride | 6.4 mg/100 cm² |
| methylpyrimidine | 0.11 mg/100 cm² |
| Developing layer of fibrous structure | |
| The above enzyme-fiber complex | 180 mg/100 cm² |
| Triton X-100 (Rohm & Haas Co.) | 8 mg/100 cm² |
| Copoly (vinylbenzylamine-methyl acrylate) (weight ratio 5:95) | 3.6 mg/100 cm² |

On the above analytical element of the present invention, each 10 μl of aqueous cholesterol solutions with various known concentrations (5% bovine serum albumin) were spotted and incubated at 37° C. for 10 minutes, followed by measurement of reflection densities to prepare a calibration curve.

Then, three kinds of human serums with different cholesterol concentrations were prepared and each 10 μl was spotted and incubated at 37° C. for 10 minutes, and thereafter the reflection densities were converted to the cholesterol concentrations from the above calibration curve. As control, a kit for manual method "Cholesterol C-test Wako" (produced by Wako Junyaku Co., Ltd.; for measurement of total cholesterol) was used for measurement of the cholesterol concentration in the same serums. The results are shown below Table 1.

TABLE 1

|  | Analytical element of the invention | Control analytical method |
|---|---|---|
| Human serum I | 35 mg/dl | 33.5 mg/dl |
| Human serum II | 83.5 mg/dl | 84.3 mg/dl |
| Human serum III | 165.0 mg/dl | 160.5 mg/dl |

As shown in the above Table 1, the measurement results by the analytical element of the present invention were found to be fairly consistent with the results by the control analytical method.

EXAMPLE 3

Introduction of reactive groups into fibers

To a mixture of 45 g of styrene, 5 g of glycidyl methacrylate and 1.5 g of 2,2'-azobis-(2,4-dimethylvaleronitrile), there was added 20 g of a powdery filter paper C (produced by Tokyo Roshi Co., Ltd.; 300 mesh or more) for impregnation with the monomer mixture. Then, the above powdery filter paper impregnated with the monomers was added into 200 ml of an aqueous solution containing 8 g of tricalcium phosphate and 0.04 g of sodium dodecylbenzenesulfonate, and after stirring the mixture under nitrogen stream with a stirring speed of 200 rpm for 30 minutes, the contents were transferred into a 300 ml four-necked flask. The reaction was carried out under nitrogen stream at 60° C. with stirring at 300 rpm for 8 hours. The contents were cooled to room temperature, and tricalcium phosphate was decomposed with dilute hydrochloric acid and removed. After repeated washing with water, the product was filtered and dried.

From the weight gain, it was found that 0.8 g of the polymer was introduced per 1 g of fiber.

Reaction of an antibody to fiber-polymer complex

In a solution containing 99 parts by volume of 0.03M Na$_2$CO$_3$ of pH 9.5 and 1 part by volume of bovine γ-globulin (hereinafter abbreviated as anti-BGG) rabbit serum, the above fiber-polymer complex was dispersed to a solid content of 20% by weight, and the dispersion was stirred at room temperature for 24 hours to bind the anti-BGG with the complex. Then, the product was filtered and washed repeatedly with 0.15N-NaCl aqueous solution to provide an anti-BGG bound fiber.

Preparation of a fluorescent immunological analytical element

The following layers were coated on a transparent polystyrene support of a thickness of 180 μm, exhibiting only a low level of fluorescence:

| Detection layer | |
|---|---|
| Normal rabbit serum | 5 mg/100 cm$^2$ |
| The above fiber-polymer complex | 100 mg/100 cm$^2$ |
| Zeonil FSN (Du Pont) | 0.1 mg/100 cm$^2$ |
| (2) Fluorescent blocking layer | |
| The above fiber-polymer complex [including 1.5 wt. % of Paliofast Blue (BASF)] | 25 mg/100 cm$^2$ |
| (3) Diffusion and reagent layer | |
| The above fiber-polymer complex having bound anti-BGG | 40 mg/100 cm$^2$ |
| Normal rabbit serum | 1.74 mg/100 cm$^2$ |
| Zeonil FSN | 0.5 mg/100 cm$^2$ |

Using the thus prepared immunological analytical element, the test analytes having the following compositions were tested.

That is, each 10 μl of test analytes comprising 50% normal rabbit serum containing $5 \times 10^{-8}$ mole of fluorescein-labelled bovine γ-globulin and various concentrations from 0 to $10^{-5}$ mole of unlabelled bovine γ-globulin and 50% phosphate buffer isotonic saline solution was spotted on the above element, followed by incubation at 37° C. for 15 minutes.

Then, using a reflection fluorescentphotometer having an excitation filter of 490 nm and an emission filter of 515 nm, the above element was measured from the side of the support. The results are shown in Table 2.

TABLE 2

| Concentration of unlabelled BGG | Fluorescence (optional unit) |
|---|---|
| 0 | 377 |
| $2.5 \times 10^{-8}$ M | 390 |
| $\times 10^{-8}$ M | 420 |
| $1 \times 10^{-7}$ M | 473 |
| $1 \times 10^{-6}$ M | 558 |
| $1 \times 10^{-5}$ M | — |
| Buffer blank | 42 |

As shown in Table 2, the analytical element of the present invention can effectively used also in the field of immunological analysis.

We claim:

1. An analytical element for detecting a component in a liquid sample, said analytical element containing a light-transmissive and liquid-impermeable support and at least one developing layer having a fibrous structure, said fibrous structure comprising fibers which are loose and randomly entangled with each other in said at least one developing layer, said fibers having a size of from 50 to 325 mesh,
    said at least one developing layer containing at least one interactive composition capable of reacting with said component to be detected and said interactive composition being bound to the fibers of said developing layer through a compound having a first reactive group for binding to said fibers and a second reactive group for binding to said interactive composition, and a portion of said reactive groups of said compound being bound to at least one of each other and groups in a binder or adjacent layers, thereby increasing the mechanical strength of the developing layer of fibrous structure and greatly enhancing adhesion to the adjacent layers.

2. The analytical element of claim 1 wherein said fibers are selected from the group consisting of natural macromolecular fibers and synthetic macromolecular fibers.

3. The analytical element of claim 1 wherein said first and second reactive groups are each selected from the group consisting of an epoxy group, an aldehyde group, an aziridyl group, a hydroxymethyl group, an isocyanate group, a thiol group, a carbamoyl group, a vinylsulfonyl group and precursors thereof.

4. The analytic element of claim 1 wherein a portion of said reactive groups of said compound are bound to said binder or said adjacent layers.

5. The analytical element of claim 1 wherein the compound is introduced into said developing layer by a low temperature plasma polymerization method.

6. The analytical element of claim 1 wherein the compound is introduced into said developing layer by a suspension polymerization method.

7. The analytical element of claim 1 wherein the compound is introduced into said developing layer by a radical polymerization method.

8. The analytical element of claim 1 wherein the compound is introduced into said developing layer by a photopolymerization method.

9. The analytical element of claim 1 wherein said developing layer has a thickness of 50 to 500 $\mu$m.

10. The analytical element of claim 9 wherein said developing layer has a thickness of 100 to 350 $\mu$m.

11. The analytical element of claim 1 wherein the compound having said first and second reactive groups is present in an amount of 0.1 to 100% by weight in said at least one developing layer.

12. The analytical element according to claim 11 wherein the compound having said first and second reactive groups is present in an amount of 0.5 to 85% by weight in said at least one developing layer.

13. The analytical element of claim 1 wherein said interactive composition comprises a material which reacts with said component to be detected in said liquid sample to produce a change in the electromagnetic characteristics of said liquid sample.

14. The analytical element of claim 13 wherein said interactive composition is a compound selected from the group consisting of a colorimetrically detectable compound; a phosphorimetrically detectable compound; a radiometrically detectable compound and a fluorimetrically detectable compound; and precursors thereof.

15. The interactive composition of claim 14 wherein said interactive composition is a member selected from the group consisting of an antigen, a hapten, an antibody, an antigen-antibody complex, an enzyme and precursors thereof.

16. The analytical element of claim 1 wherein the compound is introduced into said developing layer by a graft polymerization method.

17. The analytical element of claim 16 wherein the graft polymerization method is a radiation graft polymerization method.

18. The analytical element of claim 17 wherein the radiation graft polymerization method is a simultaneous irradiation graft polymerization method or a pre-irradiation graft polymerization method.

19. The analytical element of claim 1 wherein the compound having said first and second reactive groups is a copolymer of a first monomer having said first and second reactive groups with at least one second monomer selected from the group consisting of:

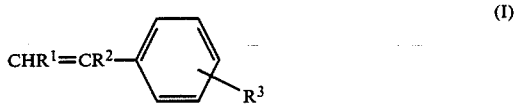

(I)

wherein each of $R^1$ and $R^2$, which can be the same or different, represents a non-interfering substituent and $R^3$ is selected from the group consisting of a hydrogen atom, a halogen atom, and a substituted or unsubstituted amino-free aliphatic or aromatic group having 1 to 10 carbon atoms;

$$CHR^6=CR^4-COOR^5 \qquad (II)$$

wherein $R^6$ has the same meaning as $R^1$ in the formula (I), $R^4$ is a hydrogen atom or a methyl group and $R^5$ represents an aryl, an alkyl, an alkaryl or an aralkyl group, each having 1 to 10 carbon atoms;

(III) polymerizable unsaturated nitrile monomers; and (IV) interparticle crosslinking monomers having two addition-polymerizable groups.

20. The analytical element of claim 19 wherein the copolymer comprises 0.1 to 30% by weight of said first monomer, and as said second monomer 0 to 99.5% by weight of a monomer having the formula (II), 0 to 99.5% by weight of a monomer having the formula (II), 0 to 99.5% by weight of a monomer having the formula (III) and 0 to 10% by weight of a monomer having the formula (IV).

21. The analytical element of claim 19 wherein the copolymer having said first and second monomers is present in an amount of 0.2 to 200% by weight in said at least one developing layer.

22. The analytic element of claim 19 wherein each of $R^1$ and $R^2$ are selected from the group consisting of a hydrogen atom, a halogen atom, and a substituted or unsubstituted amino free alkyl or aryl group having 1 to 10 carbon atoms.

23. The analytical element of claim 22 wherein the second monomer is selected from the group consisting of styrene, vinyltoluene, vinylbenzyl chloride, t-butylstyrene, acrylonitrile, methacrylonitrile, divinylbenzene, N-n-methylene-bis(acrylamide), ethylene diacrylate and ethylene dimethacrylate.

* * * * *